United States Patent [19]

Abdel-Monem

[11] 3,941,818

[45] Mar. 2, 1976

[54] 1:1 ZINC METHIONINE COMPLEXES

[75] Inventor: Mahmoud M. Abdel-Monem, Minneapolis, Minn.

[73] Assignee: Zinpro Corporation, Chaska, Minn.

[22] Filed: Aug. 20, 1973

[21] Appl. No.: 390,080

[52] U.S. Cl............ 260/429.9; 260/429 K; 260/999
[51] Int. Cl.² .......................................... C07F 3/06
[58] Field of Search ...................... 260/429.9, 429 K

[56] References Cited
UNITED STATES PATENTS
3,647,834    3/1972    Martin ............................ 260/429.9

OTHER PUBLICATIONS
Chemical Abstracts, Vol. 50, 12885c (1963).
Li et al. J.A.C.S., Vol. 77, 5225–5228 (1955).

*Primary Examiner*—Helen M. S. Sneed
*Attorney, Agent, or Firm*—Zarley, McKee, Thomte & Voorhees

[57] ABSTRACT

Novel salts are prepared wherein the cation of the salt comprises a 1:1 ratio of a complex ion formed between zinc and methionine and any suitable anion, either inorganic or organic. The novel salts have the generic formula:

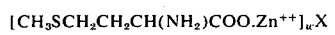

$[CH_3SCH_2CH_2CH(NH_2)COO \cdot Zn^{++}]_w X$ wherein X is an anion and $w$ is an integer equal to the anionic charge of X. These novel compounds are useful nutritional supplements, both for animals and humans, in that they provide a readily-available source of the zinc ions necessary for dietary balance. In addition, certain of the compounds falling within the formula disclosed herein have been found to have therapeutic utility in the treatment of acne and colitis.

21 Claims, No Drawings

1:1 ZINC METHIONINE COMPLEXES

BACKGROUND OF THE INVENTION

The importance of an adequate supply of zinc to the diet of both animals and humans has long been reported in the literature. Adequate dietary intake of zinc for swine, cattle, and poultry has been known for some time to be of importance. For example, when these animals do not have a dietary balance having a sufficient level of zinc ions in the diet, the animals may well develop skin conditions showing noted zinc deficiencies. For example, the skin may become sick, scaly, and inflamed. In addition, it has been reported in the literature that animals fed a diet deficient in zinc may tend to develop congenital anomalies and fibrotic changes in the esophagus. Additionally, and very importantly, an adequate level of zinc in the diets of swine, poultry, and cattle has been shown as important for healthy growth of the animals and increased weight gain.

With regard to humans, zinc deficiencies have been reported as possibly tied to arteriosclerosis, the proper growth and function of sex organs, and the ability of skin wounds to heal fast and properly.

While the importance of an adequate zinc level in the diet of both animals and humans has been known and reported for sometime, maintenance of adequate zinc levels in the dietary intake has not necessarily been easy to achieve. Moreover, dietary supplementation by utilization of conventional salts of zinc, such as zinc chloride, seems to be inadequate. This is so because the zinc exists in a form which is not readily absorbed from the gastrointestinal tract and therefore may not be distributed and utilized effectively in the body.

Accordingly, it is an object of this invention to provide novel zinc compounds wherein the zinc is in a form which can be readily absorbed after ingestion by animals and readily distributed and utilized in order to provide adequate zinc levels for proper health, weight gain, and dietary balance of animals.

Yet, another object of this invention is to provide a process for making novel zinc compounds which is simple to perform and can be economically utilized in large-scale plant practice to prepare the novel zinc compounds of this invention in bulk for ready utilization in large quantities to supplement the diets of animals and humans.

The method of accomplishing these and other objects will become apparent from the following description of the invention.

SUMMARY OF THE INVENTION

This invention relates to the preparation of novel zinc compounds. The novel zinc compounds have the formula:

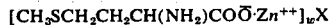

wherein X is an anion and $w$ is an integer equal to the anionic charge of X. These compounds all contain a 1:1 ratio complex of zinc and methionine as the cation. Such compounds, it is believed because of a complex formed between the zinc and methionine, are in a form which can be readily absorbed, distributed, and utilized within the biochemical system of animals and humans. They function as a readily-available source of zinc for dietary supplementation.

The invention also relates to a new, simple, and economically feasible process for making the above-described compounds.

Detailed Description of the Invention.

It is important to note that the compounds of this invention are referred to herein as "zinc methionine complexed salts." These salts are to be carefully distinguished from conventional salts such as, for example, zinc sulphate and zinc chloride, which contain only an electrostatic attraction between the cation and the anion. The complexed salts of this invention differ from conventional salts in that while they have an electrostatic attraction between the cation and the anion, there is also a coordination bond formed between the zinc and the amino moiety of the amino acid methionine. The zinc methionine complexed salts have the formula:

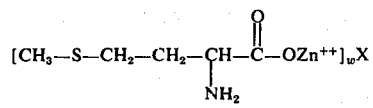

wherein X is an anion and w is an integer equal to the anionic charge of X. The cation of these complexed salts is represented by the bracketed material in the above formula and represents a 1:1 complex of zinc and methionine. Sterically, the cation moiety can be represented as follows:

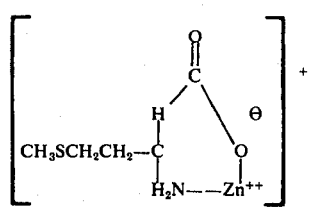

As can be seen from this formula, the five-membered ring formation exists wherein the zinc ion is complexed by coordinate bond with the amine moiety, and electrostatic attraction with the carboxylic acid moiety of the methionine. In addition, the complex is formed by a 1:1 ratio of methionine molecules and zinc ions with each zinc ion becoming complexed with one methionine molecule. Providing 1:1 complex ions of the zinc and methionine has been found of great importance in insuring gastro-intestinal absorbtion of the zinc and its subsequent distribution and effective utilization of the zinc.

In addition, certain of these compounds, and in particular, zinc methionine acid sulphate, and zinc methionine chloride have been found to have some therapeutic effect in the treatment of acne, colitis and other epidermal disorders.

In the above-described formula X represents the anion. The selection of an anion is not critical. The anion can be an inorganic anion, an organic anion, a monovalent anion, a divalent anion, or a polyvalent anion. However, in order to have the molecules of the salt balanced electrostatically, $w$ is a whole number integer equal to the anionic charge of the anion X.

Preferably, the source of the anion, X, is an inorganic acid. Suitable inorganic anions can be found in the halogen acids family, the sulphates, and the phosphates. Preferably, where the anion is an inorganic anion, it is selected from the group consisting of monovalent anions, such as halides, hydrogen sulphate, and dihydrogen phosphate. Utilization of monovalent anions selected from the above group is preferred because of the resulting ready solubility of the zinc methionine complexed salts and because of the readily-available sources of common inorganic anions such as the halides, hydrogen sulphate, and dihydrogen phosphate. Most preferably, the anion is selected from the group consisting of chloride and hydrogen sulphate or acid sulphate, the latter two terms being utilized herein interchangeably.

As heretofore briefly mentioned, the anion can also be an organic anion moiety derived from an organic acid. It can be derived from simple aliphatic carboxyllic acids, both monobasic carboxyllic acids and dibasic carboxyllic acids. For example, the anion can be acetate or propionate, or where the acid is a dibasic acid, succinate or adipate. In addition, the acid source can be substituted aliphatic acids, both monobasic and dibasic, such as, for example, chloroacetic acid. The acid source of the anion may also be aromatic acids such as, for example, benzoic acid. It can also be aralkyl acids, both substituted and unsubstituted.

Where organic acid sources are utilized as the source of the anion for the salts of this invention, it is preferred that the source be a monobasic carboxyllic acid and that the acid be either acetic acid, propionic, or benzoic.

Surprisingly, a simple, straight-forward and, importantly, economically feasible process of preparing these zinc methionine complexed salts of this invention in a form readily utilizable for dietary supplementation has been developed. For purposes of clarity of description of the invention and conciseness, the method will be described only with relationship to preparing the two most preferred compounds, zinc methionine acid sulphate and zinc methionine chloride. It should be understood, however, that the method can easily be modified for preparation of other zinc methionine complexed salts such as zinc methionine diacid phosphate, zinc methionine acetate, zinc methionine propionate, zinc methionine benzoate, and the like. Zinc methionine acid sulphate and zinc methionine chloride are preferred compounds because they can be easily prepared and, importantly, have been found to have special preferred efficacy in dietary ingestion and body distribution and utilization. The method will first be described in connection with the preparation of zinc methionine acid sulphate.

In accord with the process of this invention, zinc sulphate, either in an anhydrous form or in a hydrated form is reacted with methionine at a pH of 7 or less. It is important that the pH be controlled to either neutral or acid conditions because if the pH is allowed to become basic, the resulting product will be a 1:2 complex of methionine and zinc which is insoluble in water. Preferably, the reactants, zinc sulphate and methionine are used in equimolar quantities. Utilization of equimolar quantities insures complete reaction with a minimum of side reactions, or excess ingredients. It is preferred that the zinc sulphate be hydrated zinc sulphate, in that little water is needed. Where anhydrous zinc sulphate is utilized, it is preferred that a quantity of water be added to the reaction ingredients about equal to the weight of zinc sulphate and methionine.

The product, zinc methionine acid sulfate, can be conveniently obtained from the reaction solution by the addition of an organic solvent such as isopropyl alcohol, acetone or ethyl alcohol. Alternatively, the reaction solution could be dried using conventional drying methods such as hot air oven, spray drying, or freeze drying to provide a white, solid, uniform free flow appearing powdered form of zinc methionine acid sulphate.

The reaction can be carried out under similar conditions of pH, to prepare zinc methionine chloride by substituting zinc chloride as an initial reaction ingredient for the zinc sulphate previously described herein. However, the resulting product is zinc methionine chloride, which is very soluble in water and is obtained as a syrupy concentrated aqueous solution.

An important feature of the 1:1 complexed salts, having zinc methionine complexes as a cation and associated with suitable anions, is that the stability of the zinc methionine complex is such that after absorbtion, the zinc can be readily utilized within an animal body's biochemical systems. This is to be contrasted from complexes of zinc and other complexing agents such as ethylenediamine tetraacetic acid. In these cases the stability of the complexes is so great that the zinc is not readily released and is therefore not available for distribution and utilization within the animal's body. In fact, there is a tendency for ethylenediamine tetraacetic acid to "draw" zinc molecules from the body and to complex them with the resulting complex being excreted. Thus, extremely strong coordinate covalent bonds, such as those formed by ethylenediamine tetraacetic acid, can actually enhance zinc deficiency in an animal's body bio-chemical system.

The following examples are offered to further illustrate the product and process of this invention.

EXAMPLE 1.

hydrated Hydrated sulphate ($ZnSO_4 \cdot 7H_2O$, 28.75g, 0.1 mol) and methionine (14.9g, 0.1 mol) were dissolved in 100 ml of water by the aid of gentle heat. The hot solution was treated with 3,000 ml of acetone, stirred vigorously for 10 minutes and allowed to cool. A white precipitate was formed, filtered and dried. The weight of the precipitate was 31.0 g. The precipitate was analyzed by routine analytical procedures and was found to contain 20.80% zinc and 47.45% methionine. This will reveal a proper ratio of zinc and methionine to indicate a 1:1 ratio, indicating the formation of a 1:1 complex. In addition, the sample was analyzed by infrared analysis and an examination of the absorption peaks indicated the absence of a strong peak at 2100 reciprocal centimeters, which is characteristic of alpha amino acids. In addition, there was a noted absence of the characteristic peaks of methionine itself. The different peak structures of the product from the peak structures of the reactants indicated the formation of a 1:1 complex of zinc and methionine. Finally, the resulting product was titrated with 0.1 normal sodium hydroxide and the titration curve was compared with a known titration curve for DL methionine and zinc sulphate. The titration curve proved to be different than the titration curve for either zinc sulphate or DL methionine, indicating formation of the complex salt.

EXAMPLE 2.

Hydrated zinc sulphate ($ZnSO \cdot 7H O$, 57.5 g 0.2 mol) and methionine (29.84 g, 0.2 mol) were mixed thoroughly in an evaporating dish. The mixture was heated on a steam bath to form a paste. Heating was continued for 60 minutes and the paste was transferred into a hot air oven and dried at 90° C. for 20 hours. The resulting product weighed 63.3 g. Quantitative analysis revealed the product was comprised of 20.37% zinc and 46.5% methionine. This indicated a proper ration of zinc to methionine for a 1:1 complex of zinc methionine. Further analysis by infra-red analysis and titration curve analysis indicated the presence of zinc methionine acid sulphate as per the previous example. The product was a dry, free-flowing powder.

While the paste of this example was hot air oven dried, other preparations have been prepared where the resulting solutions were spray-dried in a spray dryer at a temperature of about 400°F to yield a dry free-flowing powder.

EXAMPLE 3.

Zinc chloride (Zn $Cl_2$, 68.0g, 0.5 mol) was dissolved in water (68.0 g) and the solution was heated to 90° c. Methionine (74,bg, 0.5 mol) was added and the temperature was kept at 90° C. for one hour to provide zinc methionine chloride solution. The product contained 21.2% zinc and 53.9% methionine. Quantitative and instrumental analysis as previously described revealed the presence of a 1:1 complex salt of zinc methionine chloride.

EXAMPLE 4.

Methionine (74.6g, 0.5 mol) was dissolved in a 165 ml of 6.08 N N hydrochloric acid and zinc oxide (40.65g) was added. The mixture was heated at 90° C. for one hour to provide zinc methionine chloride solution. The product contained 19.9% zinc and 44.0% methionine. The presence of zinc methionine chloride was confirmed by quantitative and instrumental analysis.

EXAMPLE 5.

Methionine zinc sulfate (6.2 g, 0.05 mol) was dissolved in 100 ml of $H_2O$. The solution was heated to boiling and a solution of barium acetate (5.1 g, 0.05 mol) in 20 ml of water was added dropwise with stirring, a voluminous precepitate was formed. The mixture was treated with a solution of methionine zinc sulfate until no further pption of $BaSO_4$ was observed. The solution was boiled for ten minutes and filtered. The filtrate was evaporated to dryness to afford a white powder. The product contained 23.4% zinc and 57.7% methionine. Quantitative and instrumental analysis as previously described revealed the presence of zinc methionine acetate.

EXAMPLE 6.

Zinc oxide (8.13 gr) was dissolved in a mixture of 48% hydrobromic acid (33.7gr) and water (15.0 gr). Methionine (15.0 gr) was added and the solution was heated at 95° C. for 15 minutes. The mixture was evaportated to dryness. The residue was dried in the oven and the product contains 17.2% zinc and 36.7% methionine. Quantitative and instrumental analysis revealed the presence of zinc methionine bromide.

I claim:

1. Zinc methionine, complexed salts of the formula:

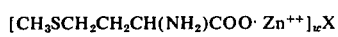

wherein X is an organic monovalent anion of a monobasic carboxylic acid selected from the group consisting of acetic acid, propionic acid, and benzoic acid, and w is an integer equal to the anionic charge of X.

2. Zinc methionine, complexed salts of the formula:

wherein X is an inorganic anion selected from the group consisting of halides, sulfates, and phosphates, and w is an integer equal to the anionic charge of X.

3. A method of preparing zinc methionine acid sulphate comprising,
   adding together at a pH of 7 or less zinc sulphate and methionine to provide a reaction mixture, and
   heating said reaction mixture at a temperature higher than room temperature but not exceeding the boiling point of said reaction mixture.

4. A method of preparing zinc methionine chloride comprising,
   adding together at a pH of 7 or less zinc chloride and methicnine to provide a reaction mixture, and
   heating said reaction mixture at a temperature higher than room temperature but not exceeding the boiling point of said reaction mixture.

5. The complexed salts of claim 2, wherein X is a monovalent anion.

6. Zinc methionine acid sulphate.

7. Zinc methionine chloride.

8. The salts of claim 1, wherein the salt is the compound zinc methionine acetate.

9. The salt of claim 1, wherein the salt is the compound zinc methionine propionate.

10. The process of claim 3, wherein the zinc sulphate is hydrated zinc sulphate.

11. The process of claim 3, wherein the reaction is conducted in the presence of added water.

12. The process of claim 11, wherein the amount of water is about equal to the combined weight of the zinc sulphate and methionine.

13. The process of claim 3, wherein the amount of zinc sulphate and methionine employed are equimolar quantities.

14. The process of claim 3, wherein the reaction is conducted in the presence of a solvent selected from the group consisting of acetone, isopropyl alcohol, and ethyl alcohol.

15. The process of claim 11, wherein the product is spray-dried to provide a free-flowing powder.

16. The process of claim 4, wherein zinc chloride is heated to at least 90° C.

17. The process of claim 4, wherein the reaction is conducted in the presence of added water.

18. The process of claim 17, wherein the amount of water is about equal to the combined weight of the zinc chloride and methionine.

19. The process of claim 4, wherein the amount of zinc chloride and methionine employed are equimolar quantities.

20. The process of claim 4, wherein the reaction is conducted in the presence of a solvent selected from the group consisting of acetone, isopropyl alcohol, and ethyl alcohol.

21. The salts of claim 5 wherein said sulfate is hydrogen sulfate and said phosphate is dihydrogen phosphate.

* * * * *